US 10,405,815 B2

(12) United States Patent
Choi (10) Patent No.: US 10,405,815 B2
(45) Date of Patent: Sep. 10, 2019

(54) X-RAY IMAGING DEVICE

(71) Applicants: VATECH Co., Ltd., Gyeonggi-do (KR); VATECH EWOO Holdings Co., Ltd., Gyeonggi-do (KR)

(72) Inventor: Sungil Choi, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 258 days.

(21) Appl. No.: 15/500,017

(22) PCT Filed: Jul. 24, 2015

(86) PCT No.: PCT/KR2015/007722
§ 371 (c)(1),
(2) Date: Jan. 27, 2017

(87) PCT Pub. No.: WO2016/018002
PCT Pub. Date: Feb. 4, 2016

(65) Prior Publication Data
US 2017/0245812 A1    Aug. 31, 2017

(30) Foreign Application Priority Data
Jul. 28, 2014   (KR) .................. 10-2014-0095717

(51) Int. Cl.
*A61B 6/14*    (2006.01)
*A61B 6/00*    (2006.01)
(Continued)

(52) U.S. Cl.
CPC .................. *A61B 6/14* (2013.01); *A61B 6/00* (2013.01); *A61B 6/032* (2013.01); *A61B 6/4435* (2013.01);
(Continued)

(58) Field of Classification Search
CPC .... A61B 6/00; A61B 6/03; A61B 6/14; A61B 6/032; A61B 6/5205; A61B 6/4435;
(Continued)

(56) References Cited

U.S. PATENT DOCUMENTS 8,396,186 B2 *  3/2013  Tomoe ..................... A61B 6/14
                                                         378/39
8,855,262 B2 * 10/2014  Takemoto ................ A61B 6/02
                                                         378/197
(Continued)

FOREIGN PATENT DOCUMENTS

EP        1752100 A2     2/2007
EP        2517628 A1    10/2012
(Continued)

OTHER PUBLICATIONS

European Patent Office, Supplementary European Search Report of corresponding EP Patent Application No. 15827868, dated Mar. 28, 2018.

*Primary Examiner* — Jurie Yun
(74) *Attorney, Agent, or Firm* — IP Legal Service, LLC (57) ABSTRACT

Provided is an X-ray imaging device for radiographing an object. The X-ray imaging device includes a generator configured to emit X-rays, a sensor unit configured to detect the X-rays using at least one sensor, a gantry having the generator and the sensor unit facing with the object therebetween, and a sensor moving part provided in the sensor unit and configured to move the sensor while the gantry rotates about a rotating axis.

10 Claims, 4 Drawing Sheets

(51) Int. Cl.
*A61B 6/03* (2006.01)
*G01T 1/161* (2006.01)
*A61B 6/06* (2006.01)

(52) U.S. Cl.
CPC ............ *A61B 6/5205* (2013.01); *G01T 1/161* (2013.01); *A61B 6/06* (2013.01)

(58) Field of Classification Search
CPC .. A61B 6/035; A61B 6/52; A61B 6/44; A61B 6/587; G01T 1/161; G01N 23/046; G01N 2223/419
USPC ...... 378/4, 11, 19, 38, 39, 40, 168, 170, 196
See application file for complete search history.

(56) References Cited

U.S. PATENT DOCUMENTS

2007/0030952 A1   2/2007   Sa et al.
2010/0074403 A1   3/2010   Inglese et al.
2012/0243762 A1   9/2012   Kanerva et al.
2012/0275563 A1   11/2012  Manak et al.
2015/0265237 A1   9/2015   Keeve et al.
2016/0213336 A1   7/2016   Kim et al.

FOREIGN PATENT DOCUMENTS

| JP | 2010-046486 A | 3/2010 |
| KR | 10-2009-0053768 A | 5/2009 |
| KR | 10-2009-0130719 A | 12/2009 |
| KR | 10-2010-0115000 A | 10/2010 |
| KR | 10-1000315 B1 | 12/2010 |
| KR | 10-2012-0107438 A | 10/2012 |
| KR | 10-2013-0003259 A | 1/2013 |
| KR | 10-1396663 B1 | 5/2014 |
| KR | 10-2015-0024706 A | 3/2015 |
| KR | 10-2015-0062521 A | 6/2015 |
| WO | 2014/064042 A1 | 5/2014 |

* cited by examiner

X-RAY IMAGING DEVICE

CROSS REFERENCE TO RELATED APPLICATIONS

This application is a National Stage Patent Application of PCT International Patent Application No. PCT/KR2015/007722 (filed on Jul. 24, 2015) under 35 U.S.C. § 371, which claims priority to Korean Patent Application No. 10-2014-0095717 (filed on Jul. 28, 2014), the teachings of which are incorporated herein in their entireties by reference.

TECHNICAL FIELD

The present invention relates generally to an X-ray imaging modality. More particularly, the present invention relates to an X-ray imaging device and an X-ray imaging method that can provide a three-dimensional X-ray image of a field of view having a desired size and shape by using a narrow-width sensor and low-dose X-ray exposure.

BACKGROUND ART

X-rays are attenuated according to an X-ray attenuation coefficient, such as photoelectric effect, Compton scattering, and the like, of a substance placed in a path of the X-rays.

X-ray imaging modality is radiography using permeability of X-rays, in which an X-ray image of an inner structure of a subject is obtained based on an amount of attenuation that is accumulated in the process of the X-rays passing through the subject. To achieve this, an X-ray imaging device includes: an X-ray source emitting X-rays toward a subject; an X-ray sensor disposed to face the X-ray source with the subject therebetween, and configured to receive the X-rays having passed through the subject; and an image processor configured to produce an X-ray image of a field of view (FOV) by using a detection result of the X-ray sensor.

Meanwhile, recently, X-ray imaging modality is being replaced with digital radiography (DR) using a digital sensor thanks to the development of semiconductor and information processing technologies, and an X-ray imaging method has also been developed in various ways.

As an example, a dental X-ray panoramic image is obtained through following process: radiographing by moving the X-ray source and the X-ray sensor along a subject, namely, a jawbone of an examinee while the X-ray source and the X-ray sensor face each other; and showing a transmission image by joining the radiographs and spreading arrangement relationship of a tooth and a tissue therearound of a desired focus layer on a jawbone trajectory. To achieve this, the X-ray source and the X-ray sensor perform rotational movement along a rotating axis therebetween within a predetermined angular range, and perform linear movement in forward and backward directions of the examinee within a predetermined length range.

The X-ray panoramic image is used as a standard image, which is the most familiar to dentists, since the entire arrangement relationship of a tooth and tissue therearound can be easily identified. However, it is problematic in that to obtain the X-ray panoramic image, a multi-axis drive system is required to link the rotational movement with the linear movement of X-ray source and the X-ray sensor.

As another example, a dental X-ray computed tomographic (CT) image is obtained through following process: radiographing by rotating the X-ray source and the X-ray sensor along a subject, namely, a head of an examinee while the X-ray source and the X-ray sensor face each other; and showing a three-dimensional X-ray image of a field of view including the head by reconstructing the radiographs. To achieve this, the X-ray source and the X-ray sensor rotates along a rotating axis passing by a subject within a predetermined angular range while facing each other.

The X-ray CT image is capable of not only displaying a three-dimensional X-ray image of a subject, but also accurately and clearly displaying a tomographic image according to desired location and direction, whereby it is used in fields that require high precision, such as implant procedures, etc. However, it is problematic in that radiation dose irradiated to an examinee is high to obtain a general X-ray CT image, and an expensive X-ray sensor having a large area is required.

To be more specific to the latter, when performing a general X-ray CT, the sensor should receive X-rays of the entire area having passed through a field of view in all directions. Accordingly, a sensor having an area much larger than that of the sensor for a panoramic X-ray image is required.

As an example, in the case of obtaining an X-ray CT image of a field of view having a first height $t1$ and a first width $w1$ by using a cone beam X-ray imaging method that is mainly used in dental fields, assuming that the rotating axis between the X-ray source and the X-ray sensor passes by a center of the field of view, a second height $t2$ of the sensor should be the same as or more than a value of a magnification ratio*the first height $t1$ (that is, $t2 \geq$ magnification ratio*$t1$), wherein magnification ratio is defined as a distance ratio of a distance between the X-ray source and the rotating axis to a distance between the X-ray source and the X-ray sensor; and a second width $w2$ of the sensor should be the same as or more than a value of the magnification ratio*the first width $w1$ (that is, $w2 \geq$ magnification ratio*$w1$), whereby it is possible to receive the X-rays of the entire area having passed through the field of view. Here, if necessary, a half beam X-ray imaging method can be used, which is configured to reduce the second width of the sensor to a value of a maximum magnification ratio*$(w1)/2$ by using an asymmetric X-ray beam covering more than a half of the field of view.

However, regardless of the imaging methods, an area of a sensor for X-ray CT is large. Further, cost of a general sensor increases dramatically according to an area thereof, so an X-ray CT imaging apparatus is problematic in that a sensor having a large area is required. Accordingly, the cost thereof increases due to size of the sensor.

DISCLOSURE

Technical Problem

Accordingly, the present invention has been made keeping in mind the above problems occurring in the related art, and the present invention is intended to propose an X-ray imaging device and an X-ray imaging method that can provide a three-dimensional X-ray image of a field of view having a desired size and shape by using a narrow-width sensor and low-dose X-ray exposure compared to a conventional X-ray CT apparatus including a half beam method.

The present invention is further intended to propose an X-ray imaging device that can expand the field of view or select the same to have a free-form shape by using a single fixed rotating axis without adding or moving a physical rotating axis between an X-ray source and an X-ray sensor, and can even provide a panoramic image.

Technical Solution

In order to achieve the above object, according to one aspect of the present invention, there is provided an X-ray imaging device including: a generator and a sensor unit facing each other with a field of view therebetween; a gantry configured to rotate the generator and the sensor unit that face each other, about a rotating axis between the generator and the sensor unit; at least one sensor provided in the sensor unit, and configured to detect X-rays; a sensor moving part provided in the sensor unit, and configured to move the sensor in a direction of a rotation trajectory of the sensor unit or in a tangential direction of the rotation trajectory when the generator and the sensor unit are rotated about the rotating axis; and an image processor configured to produce a three-dimensional X-ray image of an entire area of the field of view, by using a detection result of the sensor.

Herein, when a width of the field of view is w1, a width w2 of the sensor is less than a value of a magnification ratio*a first width (w1)/2 (that is, w2<magnification ratio*(w1/2)), and the magnification ratio may be defined as a distance ratio of a distance between the generator and the rotating axis to a distance between the generator and the sensor.

The sensor moving part may move the sensor at a constant speed or at an accelerated speed.

The generator may emit the X-rays toward the sensor. In this case, the generator may include: an X-ray source emitting the X-rays; and a collimator adjusting the X-rays to correspond to the sensor. The X-ray imaging device may further include a generator moving part configured to move or rotate the generator such that the generator emits the X-rays toward the sensor.

In order to achieve the above object, according to another aspect of the present invention, there is provided an X-ray imaging method, in which a generator and a sensor unit facing each other with a field of view therebetween, a gantry configured to rotate the generator and the sensor unit that face each other, about a rotating axis between the generator and the sensor unit, and at least one sensor provided in the sensor unit to detect X-rays are used, the method includes: rotating the generator and the sensor unit about the rotating axis, and moving the sensor in a direction of a rotation trajectory of the sensor unit or in a tangential direction of the rotation trajectory, simultaneously; and producing a three-dimensional X-ray image of an entire area of the field of view, by using a detection result of the sensor.

When a width of the field of view is w1, a width w2 of the sensor is less than a value of a magnification ratio*a first width (w1)/2 (that is, w2<magnification ratio*(w1/2)), and the magnification ratio may be defined as a distance ratio of a distance between the generator and the rotating axis to a distance between the generator and the sensor.

Advantageous Effects

According to the present invention having the above-described characteristics, it is possible to provide an X-ray imaging device and an X-ray imaging method that can provide an accurate three-dimensional X-ray image of a field of view having a desired size and shape, for example, a field of view having a width more than twice a width of a sensor, by using a narrow-width sensor and low-dose X-ray exposure compared to a conventional X-ray CT apparatus including a half beam method.

Further, it is possible to provide an X-ray imaging device that can expand the field of view or select the same to have a free-form shape by using a single fixed rotating axis without adding or moving a physical rotating axis between an X-ray source and an X-ray sensor, and can even provide a panoramic image.

MODE FOR INVENTION

Reference will now be made in greater detail to exemplary embodiments of the present invention, an example of which is illustrated in the accompanying drawings. Although preferred embodiments of the present invention have been described for a dental X-ray imaging device, those skilled in the art will appreciate that the present invention can be applied to all X-ray imaging devices, without departing from the scope and spirit of the invention as disclosed in the accompanying claims.

Figure 1:
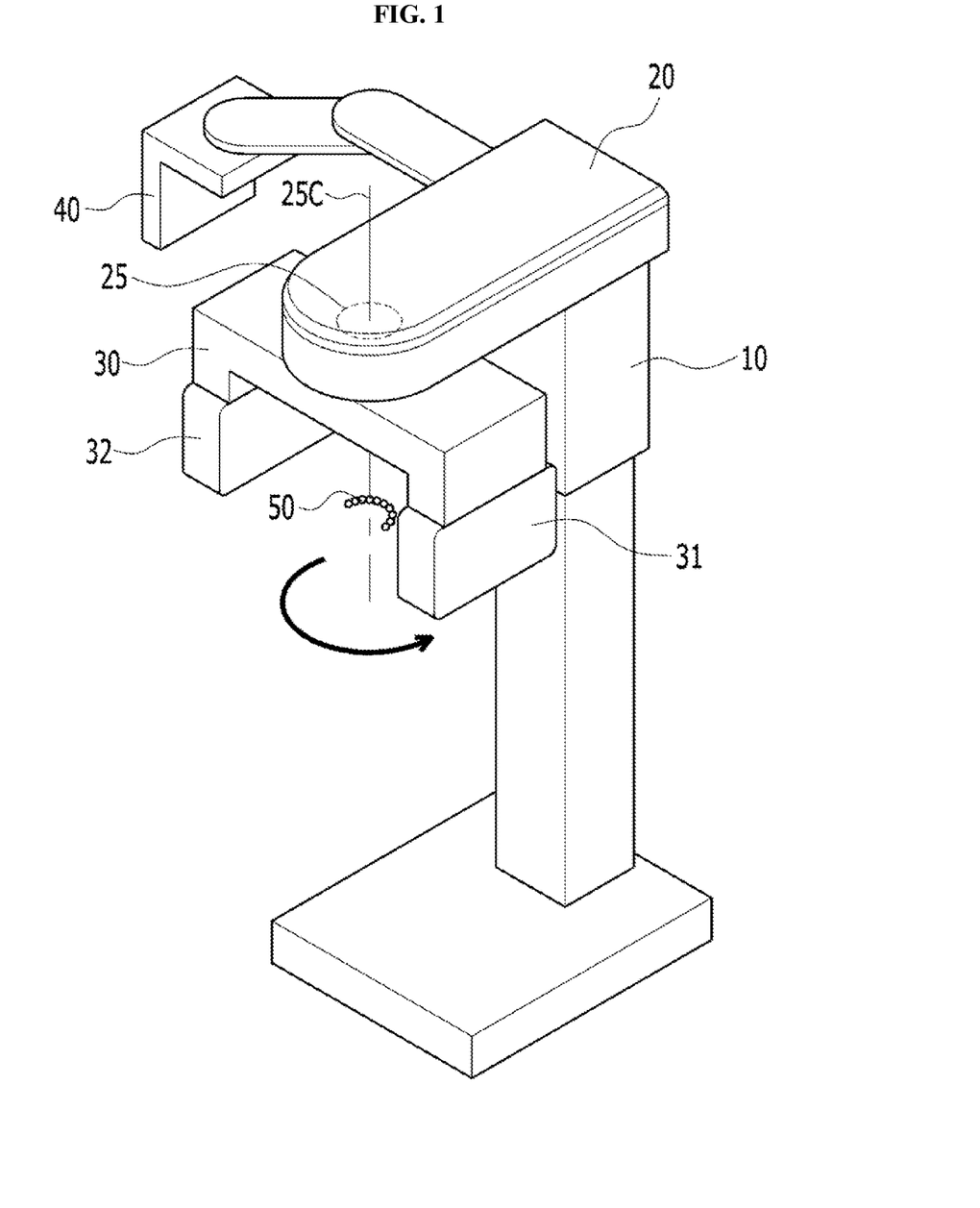
FIG. 1 is a perspective view showing an X-ray imaging device according to an embodiment of the present invention.

FIG. 1 is a perspective view showing an X-ray imaging device according to an embodiment of the present invention.

The X-ray imaging device according to the embodiment includes: a base supported on a floor; a column vertically erected from the base; and an elevation part 10 elevating along the column to correspond to a height of a subject. A rotating arm support 20 is connected to a side of the elevation part 10. The rotating arm support 20 is rotatably provided with a rotating arm 30. The rotating arm 30 includes: a generator 32 provided on a first side thereof based on a rotating axis 25C; and a sensor unit 31 provided on a second side thereof based on the rotating axis 25C to face the generator 32. When an X-ray image is taken, an extension line of the rotating axis 25C in a longitudinal direction passes a head of an examinee including a dental arch 50 as an example of a subject, and a specific location may be adjusted according to an area to be checked.

The X-ray imaging device according to the embodiment may further include an X-ray sensor unit 40 connected to the elevation part 10 directly or via the rotating arm support 20, in addition to the rotating arm 30. For example, the X-ray imaging device may be further provided with the X-ray sensor unit 40 for a cephalometric image.

Further, not shown in the drawings, the X-ray imaging device according to the embodiment includes an image processor configured to produce an X-ray image by using a detection result of the sensor unit 31, wherein the image processor may be provided in the X-ray imaging device, or may be provided apart from the X-ray imaging device and be connected to the X-ray imaging device wirelessly or by wire.

The generator 32 may include: an X-ray source configured such that, for example, electrons having high kinetic energy are collided against a metal target to emit X-rays; and a collimator adjusting an irradiation direction or an irradiation range of the X-rays. The X-ray source may be classified into two types according to electron emission method: a filament type, in which thermoelectrons are emitted by using high current; and an electric field emission type, in which field emission effect of a nanostructure, such as a carbon nanotube (CNT), is used.

The sensor unit 31 is configured to generate electric signals according to strength by locations, by receiving the X-rays having passed through the subject. In the embodiment of the present invention, a generally known technology may be widely applied according to an X-ray conversion method, for example, a direct conversion method of directly obtaining electric signals from the X-rays without an intermediate step, or an indirect conversion method of indirectly obtaining electric signals by converting the X-rays into visible rays.

The rotating arm 30 and/or the rotating arm support 20 is provided with a rotation driver 25 configured to connect the rotating arm with the rotating arm support, and to rotate the rotating arm 30 about the rotating axis 25C by using moving power. The rotation driver 25 serves to rotate the rotating arm 30 by a desired angle when the field of view (FOV) of the subject is radiographed. In other words, the X-ray imaging device of the embodiment, as a device configured to rotate the sensor unit 31 and the generator 32 with the subject therebetween, includes a gantry, wherein the gantry includes the rotating arm 30 and the rotation driver 25. Reference will be made in detail to an embodiment of overall configurations of the sensor unit 31 and the generator 32.

Figure 2:
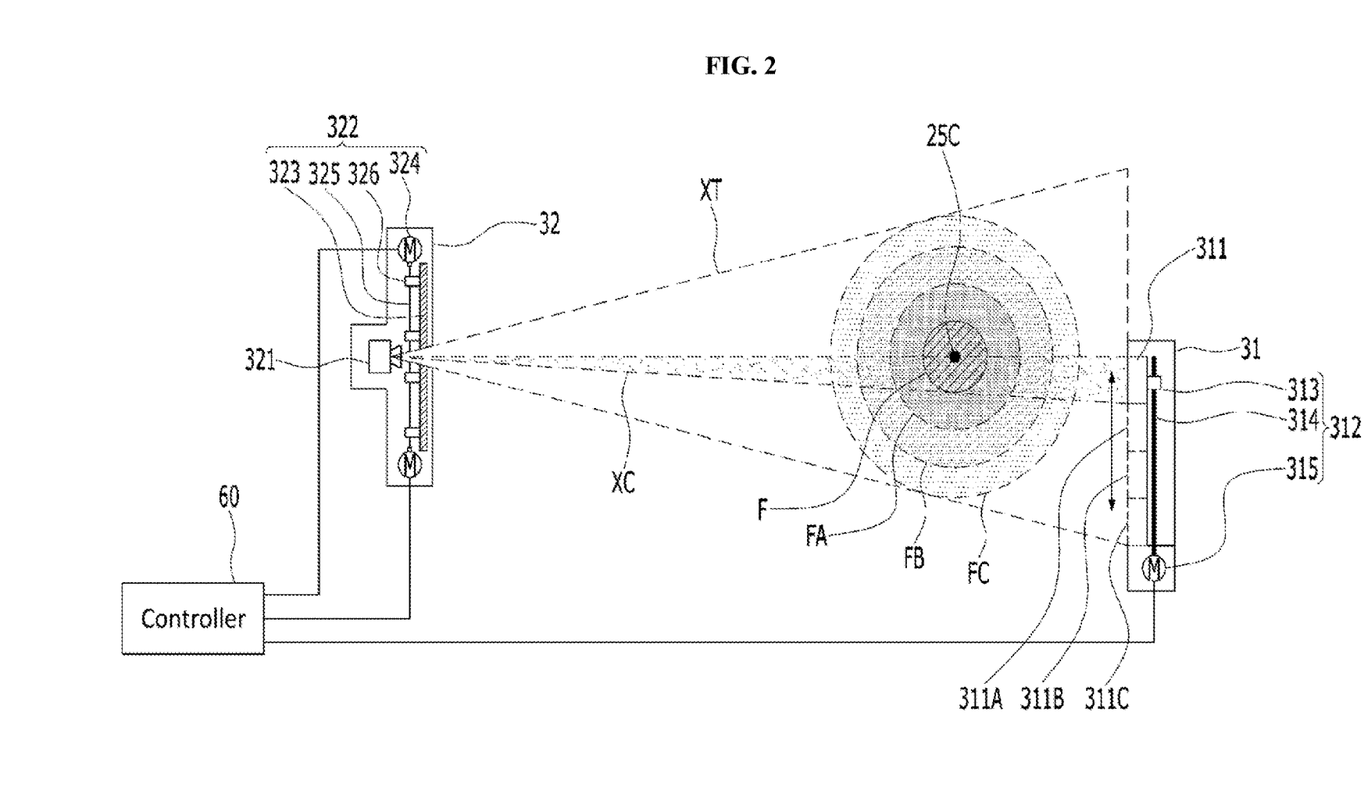
FIG. 2 is a schematic diagram showing a configuration of an X-ray imaging device according to an embodiment of the present invention and an extension of a field of view according to movement of a sensor.

FIG. 2 is a schematic diagram showing a configuration of an X-ray imaging device according to an embodiment of the present invention and an extension of a field of view according to movement of a sensor.

The sensor unit 31 is provided with at least one sensor 311 toward the generator 32. Here, when a height and a width of the field of view are t1, and w1, respectively, a height t2 of the sensor 311 is the same as or more than a value of a magnification ratio*a first height t1 (that is, t2≥magnification ratio*t1), and a width w2 of the sensor 311 is less than a value of the magnification ratio*a first width (w1)/2 (that is, w2<magnification ratio*(w1/2)).

Further, the sensor 311 is movably provided to move in a direction of a rotation trajectory of the sensor unit 31, for example, in a direction of a circular trajectory or in a tangential direction of the circular trajectory during radiography, that is, during rotation of the generator 32 and the sensor unit 31 about the rotating axis 25C; and the generator 32 emits an X-ray beam XC aimed toward the sensor 311, in conjunction with movement of the sensor 311.

In FIG. 2, concentric circles F, FA, FB, and FC that are centered on the rotating axis 25C show field of views according to a range of movement of the sensor 311. For example, in a state where the sensor 311 is fixed in the initial location marked with a solid line, an X-ray image is taken while the generator 32 and the sensor unit 31 are rotated by predetermined angles, whereby it is possible to obtain a three-dimensional X-ray image of a first field of view F that is the smallest of the concentric circles. This is the same as a conventional half beam X-ray CT apparatus.

Further, during radiography centered on the rotating axis 25C, in the case where the sensor 311 is moved from a location marked with the solid line by a width 311A thereof in a direction of the rotation trajectory or in a tangential direction of the rotation trajectory, a radius of a second field of view FA is expanded by a width of the sensor 311. Likewise, during radiography, when the sensor 311 is moved by twice 311B or three times 311C of its width, the field of view is expanded to third and fourth field of views FB and FC respectively corresponding thereto. Accordingly, even when the width of the sensor 311 is less than a value of a radius of the entire field of views F, FA, FB, and FC*a magnification ratio, it is possible to obtain a three-dimensional X-ray image of the entire field of views F, FA, FB, and FC.

For reference, in the above description and the drawings, for convenience of understanding, the sensor 311 is moved by a width of itself step by step during rotation of the generator 32 and the sensor unit 31, that is, during radiography, but it is preferred that sensor 311 is moved at a constant speed or at an accelerated speed in conjunction with the rotation of the generator 32 and the sensor unit 31 during radiography.

In other words, when rotation rates of the generator 32 and the sensor unit 31, and moving rate of the sensor 311 are adjusted properly, the field of view is actually expanded in a spiral form or in a form similar thereto; and if the rotation rates of the generator 32 and the sensor unit 31, and the moving rate of the sensor 311 are adjusted to obtain an X-ray image of an entire area of the field of view with a sufficient angular range, it is possible to realize a three-dimensional X-ray image of the entire field of view.

In terms of configuration of the device, the sensor unit 31 includes a sensor moving part 312 configured to move the sensor 311 in the direction of the rotation trajectory of the sensor unit or in the tangential direction of the rotation trajectory, within a limited range. The sensor moving part 312 may include: a motor 315 generating power; an driving shaft 314 transmitting the power; and a connector 313 connecting the sensor 311 and the driving shaft 314, wherein it is preferred that the sensor unit includes a sensor guide configured to guide movement of the sensor 311. However, the above configuration is merely an example, so various shapes and modifications are possible.

Meanwhile, the generator 32 emits the X-ray beam XC aimed to the sensor 311 in conjunction with movement of the sensor 311 by a width corresponding to the width of the sensor 311. As an example of configuration to achieve this, the generator 32 may include: an X-ray source 321 configured to emit an X-ray beam XT having a wide width to cover the range of movement of the sensor; and a collimator 322 configured to adjust the wide X-ray beam XT and to emit an X-ray beam XC that has a narrow width corresponding to the width of the sensor 311 and is aimed toward the sensor in response to movement thereof. The collimator 322 may include: at least one blade 323 configured to partially block the X-ray beam; a motor 324 configured to generate, for example, power to move the blade 323; an driving shaft 325 configured to transmit the power; and a connector 326 connecting a portion of the blade 323 with the driving shaft 325. The collimator 322 may be configured such that one blade with slits having a predetermined width, through which the aimed X-ray beam XC is passed, is driven by one motor, or two or more blades are driven by respective motors.

However, the above configuration of the generator 32 is merely an example, so various shapes and modifications are possible. For example, the generator 32 may include: an X-ray source configured to emit an X-ray beam that has a narrow width corresponding to the width of the sensor 311; and a collimator, wherein the generator 32 is physically moved and/or rotated such that an irradiation direction of the X-ray beam is in conjunction with location movement of the sensor 311. In this case, the generator 32 may further include a generator moving part for movement and/or rotation. Other than this, various shapes and modifications are possible.

Meanwhile, the X-ray imaging device according to the mentioned embodiment may include a controller 60 connected to the generator 32 and the sensor unit 31, and configured to control the same such that the generator 32 emits the X-ray beam XC aimed to the sensor 311 in conjunction with location movement of the sensor 311.

To be more specific, the controller 60 may be configured to be connected the sensor moving part 312 to control the motor 315, and configured to control a direction of the X-ray beam emitted from the generator 32, by using control signals thereof or a signal having been fed back from location information of the sensor 311. The control of the direction of the X-ray beam may be performed by controlling the motor 324 driving the collimator 322, as in the embodiment of the accompanying drawings. However, in the case where the generator 32 is configured through another configuration, a specific component receiving the control signals of the controller 60 may vary.

Further, the controller 60 may control of operation of the gantry, as well as the generator 32 and the sensor unit 31. In other words, the controller 60 may control the rotation of the gantry, the movement of the sensor, and the direction of the X-ray beam from the generator 32 to be in conjunction with each other, and detailed description thereof has been made hereinbefore.

Figure 3:
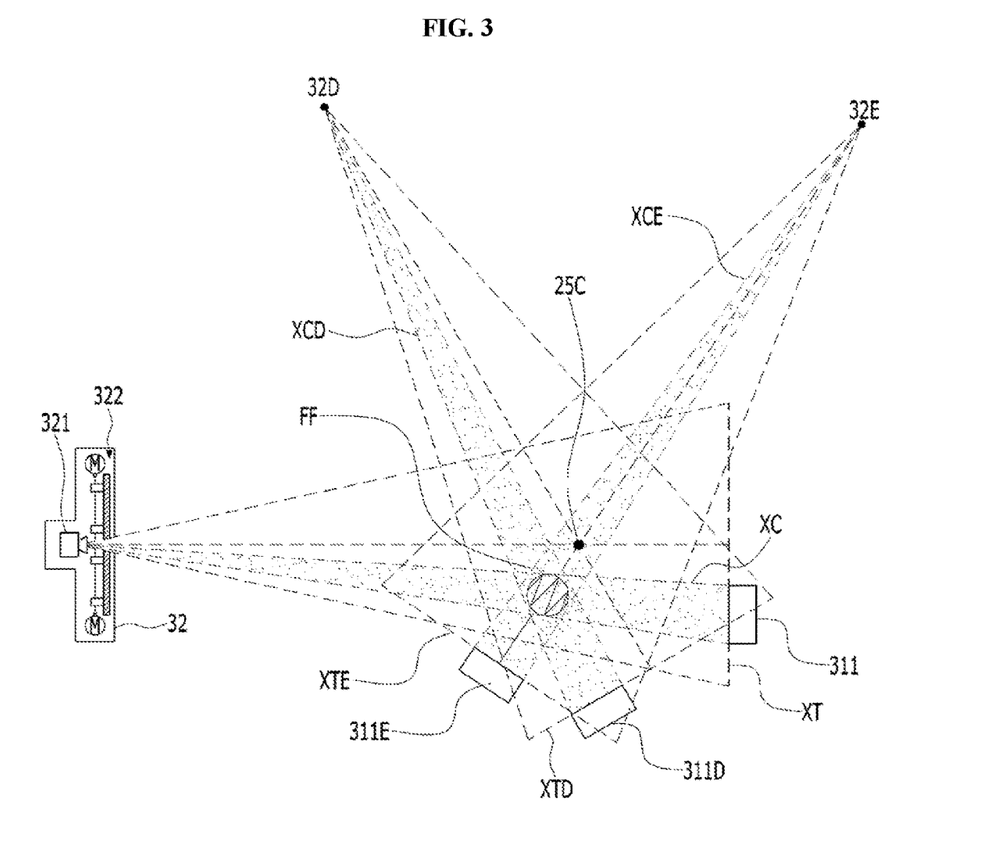
FIG. 3 is a schematic diagram showing selection of a location of the field of view by using movement of the sensor in the X-ray imaging device according to the embodiment of FIG. 2.

FIG. 3 is a schematic diagram showing selection of a location of the field of view by using movement of the sensor in the X-ray imaging device according to the embodiment of FIG. 2.

When the X-ray imaging device according to the embodiment of FIG. 2 or according to the above described modified embodiment is used, it is not only possible to expand the field of view, but also possible to freely select a location of the field of view within an available range of movement of the sensor 311. Of course, it is possible to expand the field of view by using the movement of the sensor 311, based on the selected location.

In FIG. 3, it is shown that during radiography by rotating the generator 32 and the sensor unit including the sensor 311 about the rotating axis 25C, wide X-ray beams XT, XTD, and XTE at locations 32D and 32E on the trajectory of the generator 32; narrow X-ray beams XC, XCD, and XCE; and a field of view FF generated when the wide X-ray beams and the narrow X-ray beams are overlapped with each other. When the generator 32 is disposed at the locations 32D and 32E, the sensor 311 may receive the aimed X-ray beams XC, XCD, and XCE by being moved to locations 311D and 311E within the wide X-ray beams XT, XTD, and XTE.

Figure 4:
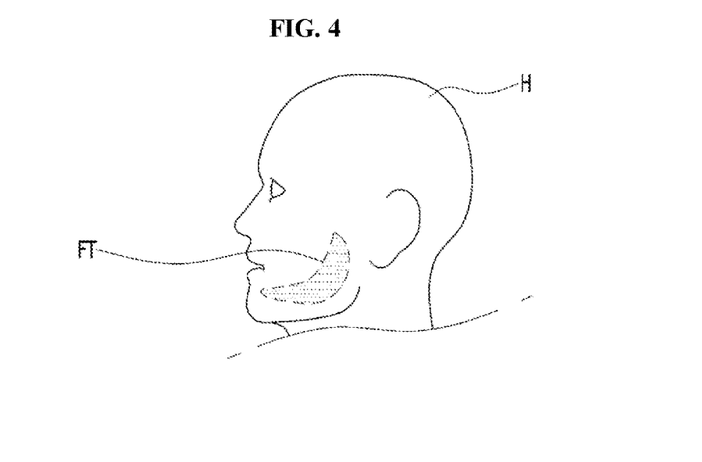
FIG. 4 is a view showing an example of the field of view having a free-form shape realized by the X-ray imaging device of the present invention.

FIG. 4 is a view showing an example of a field of view FT having free-form shape realized by the X-ray imaging device of the present invention. When the device is operated as described with reference to FIG. 3, in the state where the subject, for example, a head H of the examinee, stays still, it is possible to freely select a location of the field of view FT; and with reference to FIG. 2, through the combination of operation of the collimator in a vertical direction and the mentioned operation of the device, it is possible to expand the field of view FT having free-form size. Thereby, it is possible to obtain a three-dimensional X-ray image of the field of view FT having free-form shape corresponding to an area to be checked of the head of the examinee.

Figure 5:
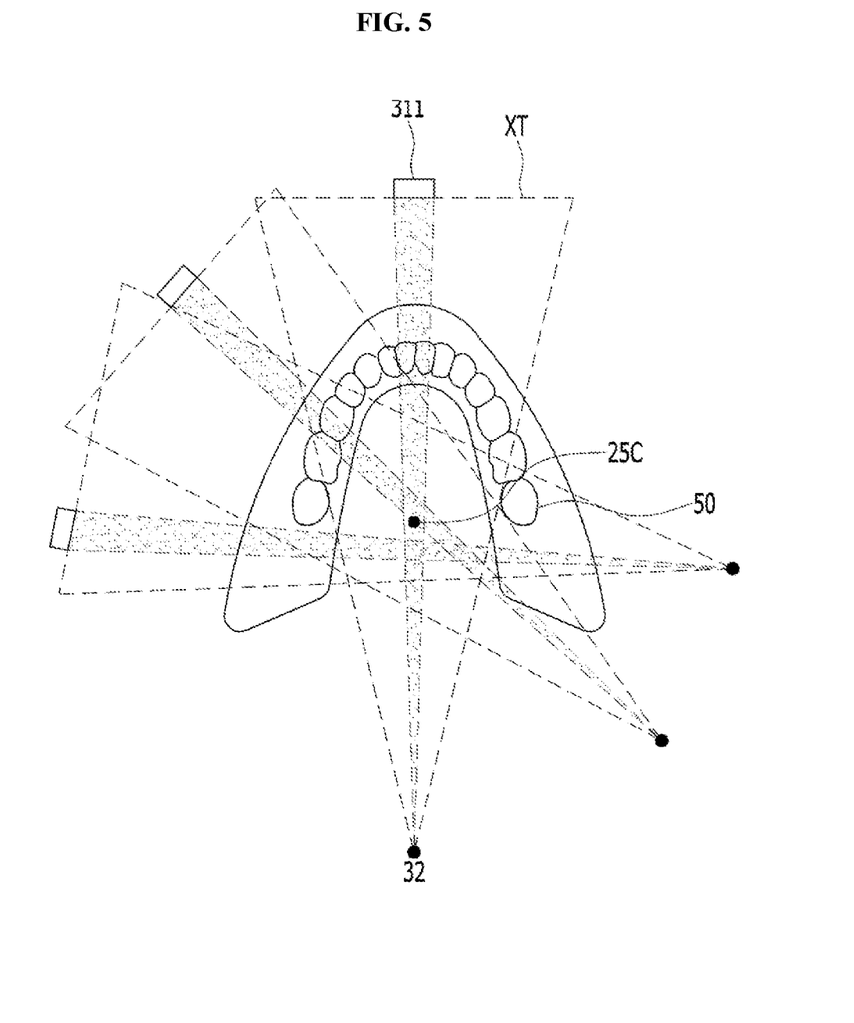
FIG. 5 is a schematic diagram showing taking an X-ray panoramic image by using an X-ray imaging device according to an embodiment of the present invention.

FIG. 5 is a schematic diagram showing taking an X-ray panoramic image by using an X-ray imaging device according to an embodiment of the present invention. As shown in FIG. 5, the generator 32 and the sensor unit including the sensor 311 are rotated about the single fixed rotating axis 25C, wherein the location of the sensor 311 is moved in the direction of the rotation trajectory of the sensor unit or in the tangential direction of the rotation trajectory, whereby it is possible to realize the same effect as moving a rotating axis in a conventional panoramic X-ray imaging apparatus, without moving the rotating axis 25C in effect.

Accordingly, the X-ray imaging device according to the present invention is capable of not only providing an X-ray CT image and a three-dimensional X-ray image, but also providing a panoramic X-ray image of focus layer corresponding to a dental arch 50 by using the mentioned properties.

The invention claimed is:

1. An X-ray imaging device for radiographing an object comprising:
   a generator configured to emit X-rays;
   a sensor unit configured to detect the X-rays using at least one sensor;
   a gantry including the generator and the sensor unit facing each other with the object therebetween; and
   a sensor moving part provided in the sensor unit and configured to move the sensor while the gantry rotates about a rotating axis,
   wherein a width of a field of view from the object is w1 and a width of the sensor is w2, w2 is less than a magnification ratio*w1/2, and the magnification ratio is a distance ratio of a distance between the generator and the rotating axis to a distance between the generator and the sensor.

2. The X-ray imaging device of claim 1, wherein the sensor moving part moves the sensor at a constant speed or at an accelerated speed.

3. The X-ray imaging device of claim 1, wherein the generator emits the X-rays toward the sensor.

4. The X-ray imaging device of claim 3, wherein the generator includes:
   an X-ray source emitting the X-rays; and
   a collimator adjusting the X-rays toward the sensor.

5. The X-ray imaging device of claim 3, further comprising:
   a generator moving part configured to move or rotate the generator such that the generator emits the X-rays toward the sensor.

6. The X-ray imaging device of claim 1, wherein the sensor moving part includes a motor, a driving shaft transmitting a power of the motor, and a connector connecting the sensor and the driving shaft.

7. The X-ray imaging device of claim 1, wherein the sensor moving part moves the sensor while radiographing the object.

8. The X-ray imaging device of claim 1, wherein the sensor moving part moves the sensor in a direction of a rotating trajectory of the sensor unit or in a tangential direction of the rotating trajectory of the sensor unit.

9. The X-ray imaging device of claim 1 further comprising:

an image processor configured to produce a three-dimensional X-ray image of the object from a detection result of the sensor.

10. The X-ray imaging device of claim 1 further comprising:
an image processor configured to produce a panoramic X-ray image of the object from a detection result of the sensor.

* * * * *